United States Patent [19]

Kleppe

[11] Patent Number: 5,349,859
[45] Date of Patent: Sep. 27, 1994

[54] METHOD AND APPARATUS FOR MEASURING ACOUSTIC WAVE VELOCITY USING IMPULSE RESPONSE

[75] Inventor: John A. Kleppe, Reno, Nev.

[73] Assignee: Scientific Engineering Instruments, Inc., Sparks, Nev.

[21] Appl. No.: 792,971

[22] Filed: Nov. 15, 1991

[51] Int. Cl.⁵ .................. G01N 29/18; G01K 11/22; G01K 11/24
[52] U.S. Cl. ......................... 73/597; 73/602; 374/117; 374/119; 367/127; 367/100
[58] Field of Search .............. 73/597, 598, 602; 374/117, 119; 367/127, 100

[56] References Cited

U.S. PATENT DOCUMENTS

| | | | |
|---|---|---|---|
| 4,162,630 | 7/1979 | Johnson | 73/194 |
| 4,772,131 | 9/1988 | Varela et al. | 374/119 |
| 4,848,924 | 7/1989 | Nuspl et al. | 374/119 |
| 5,042,303 | 8/1991 | Geluk et al. | 73/602 |
| 5,181,778 | 1/1993 | Beller | 374/119 |
| 5,197,019 | 3/1993 | Delon-Martin et al. | 73/602 |

OTHER PUBLICATIONS

Electric Circuits, Section 15.4, "The Impulse Function" by James W. Nilsson, pp. 503–509, 1983.
Acoustic Thermometry in Gases Using Pulse Techniques, M. W. Dadd, High Temp. Tech., vol. 1, No. 6, Nov. 1983.
An Acoustic Technique for Measuring Gas Temperature Distributions, Woodham and Green, 3rd Im EKO Symp., Sheffield, England, Sep. 1987.
Acoustic Temperature & Velocity Measurement in Combustion Gases, Green, 8th Intl Heat Transfer Conf., San Francisco, Cailf. 1986.
Acoustically Measuring Boiler Furnance Exit Gas Temperature Nuspl, et al., 3rd EPRI Conf. on Incipient Failure Detection in Power Plants, Phil, Pa., Mar. 1987.

Primary Examiner—Hezron E. Williams
Assistant Examiner—Rose M. Finley
Attorney, Agent, or Firm—Graham & James

[57] ABSTRACT

The transit time of acoustic waves between a generator and a receiver positioned across a fluid chamber is determined by generating acoustic waves using a self-purging pneumatic sound generator, a transducer adjacent the outlet of the sound generator, and a receiving transducer positioned away from the sound generator outlet so that the acoustic waves received by the receiving transducer pass through a portion of the fluid. The electrical signals generated by the transmitting transducer and the receiving transducer are processed to obtain the impulse response of these electrical signals, and the point of maximum value is determined. This point of maximum value corresponds to the arrival time of the acoustic waves at the receiving location. The transit time determination may be used to calculate the fluid temperature or other parameters. The pneumatic sound generator is driven by a compressed air source so that the generator is automatically purged of any contaminants in the process of generating the random acoustic noise.

19 Claims, 5 Drawing Sheets

METHOD AND APPARATUS FOR MEASURING ACOUSTIC WAVE VELOCITY USING IMPULSE RESPONSE

BACKGROUND OF THE INVENTION

This invention relates to the measurement of acoustic wave travel time in a fluid medium, with particular application to acoustic pyrometry.

Techniques are known for measuring the transit time of acoustic waves from a transmitting location to a receiving location through a fluid medium. Systems using both pulsed waves and continuous waves have been proposed and used in the past for various purposes. In pulsed systems, the transit time is typically measured by noting the time difference between the generation of an acoustic pulse at the transmitting location and the receipt of the same acoustic pulse at the receiving location. In continuous wave systems, the phase difference between the continuous wave at the transmitting location and at the receiving location provides an indirect measurement of the transit time. The transit time thus obtained is typically used to compute the velocity of the acoustic waves in the medium. In acoustic pyrometry, the computed velocity is used to compute the temperature of the fluid using a well-known relationship between acoustic velocity and temperature. For a fuller discussion of the pulsed technique see M. W. Dadd, "Acoustic Thermometry In Gases Using Pulse Techniques", High Temperature Technology, Vol. 1, No. 6, November, 1983. For a fuller discussion of the continuous wave technique see U.S. Pat. No. 4,215,582.

While both the pulsed and continuous wave techniques have been found to be useful in many applications, each is demonstrably unsuitable in extremely noisy environments in which erroneous transit time determinations occur due to the masking presence of substantial noise signals and multiple transmission paths for the acoustic wave. One example of such a noisy environment is in the field of industrial boilers, such as modern utility boilers, chemical recovery boilers and refuse boilers. Added to the noise problem is the compounding adverse effect of attenuation of acoustic waves due to scattering of the waves by temperature and velocity gradients (the latter in a moving fluid), and the masking effect of acoustic waves arriving at the receiving location via reflected boundary paths. While many efforts have been made to improve the reliability of acoustic transit time measurement in noisy environments, such efforts have not met with success to date.

SUMMARY OF THE INVENTION

The invention comprises a method and system for measuring the transit time of acoustic waves between a transmitting location and a receiving location which is highly reliable in operation, even in the extremely noisy and multi-path environments encountered in industrial applications.

From a method standpoint, the invention comprises the steps of transmitting acoustic waves through a fluid medium from a transmitting location to a receiving location, generating electrical counterpart signals corresponding to the acoustic waves at the transmitting location and at the receiving location, and determining the transit time of the acoustic waves between the transmitting location and the receiving location by obtaining the impulse response of the electrical signals and determining the point of maximum value corresponding to the arrival time of the acoustic waves at the receiving location. The acoustic waves transmitted through the fluid medium are random continuous or successive bursts each having a plurality of frequencies. For acoustic pyrometry applications, the spectrum of interest is in the band of frequencies between about 100 Hz and about 3,000 Hz.

The transit time value can be used to determine a number of parameters, such as the acoustic wave velocity in the fluid medium, the velocity of the medium itself (for a moving medium), and the temperature of the fluid medium.

From a system standpoint, the invention comprises a transmitter transducer for generating random acoustic waves for transmission through the fluid medium from a transmitting location to a receiving location, means for producing electrical signals corresponding to the acoustic waves generated by the transducer, a receiver transducer for sensing the acoustic waves arriving at the receiving location and for producing electrical signals corresponding to the received acoustic waves, and computing means for receiving the electrical signals from the producing means and the receiver transducer and for determining the transit time of the acoustic waves between the transmitting location and the receiving location by obtaining the impulse response of the electrical signals and determining the point of maximum value corresponding to the arrival time of the acoustic waves at the receiving location. The transmitting transducer is preferably a pneumatic generator powered by a suitable compressed air source and operated in a time sequential fashion in order to generate continuous or successive bursts of random acoustic waves.

The invention has been found to provide particularly improved results in extremely noisy environments, such as those found in industrial boiler applications, while at the same time providing the known advantages attendant with non-invasive acoustic pyrometric techniques. Also, the pneumatic embodiment of the transmitting transducer provides automatic purging of contaminants in the sound generating path without adversely affecting the ability of the system to obtain the transmit time.

For a fuller understanding of the nature and advantages of the invention, reference should be had to the ensuing detailed description, taken in conjunction with the accompanying drawings.

DESCRIPTION OF THE PREFERRED EMBODIMENT

Figure 1:
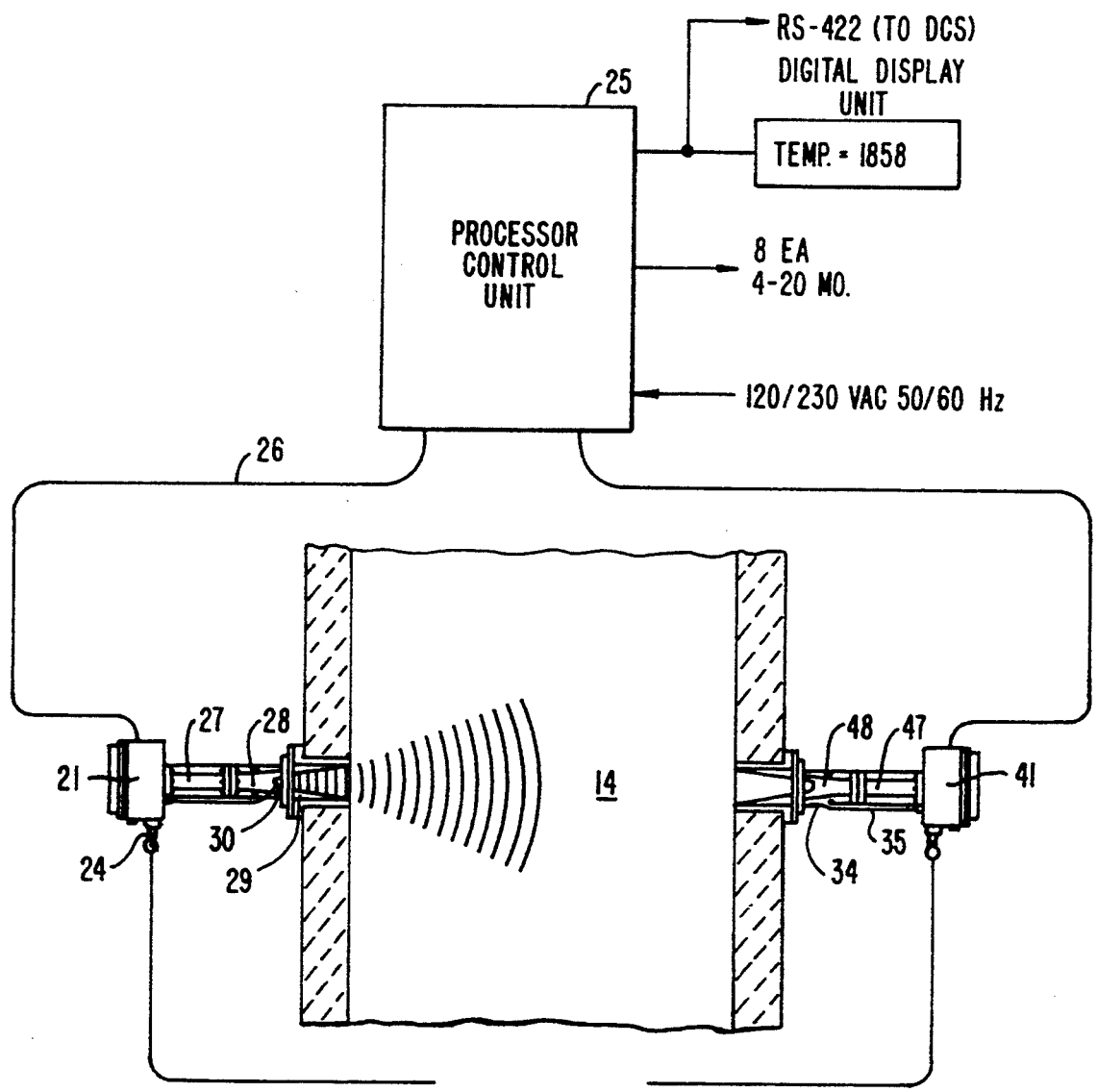
FIG. 1 is a schematic diagram illustrating the preferred embodiment of the invention applied to acoustic pyrometry.
Figure 2:
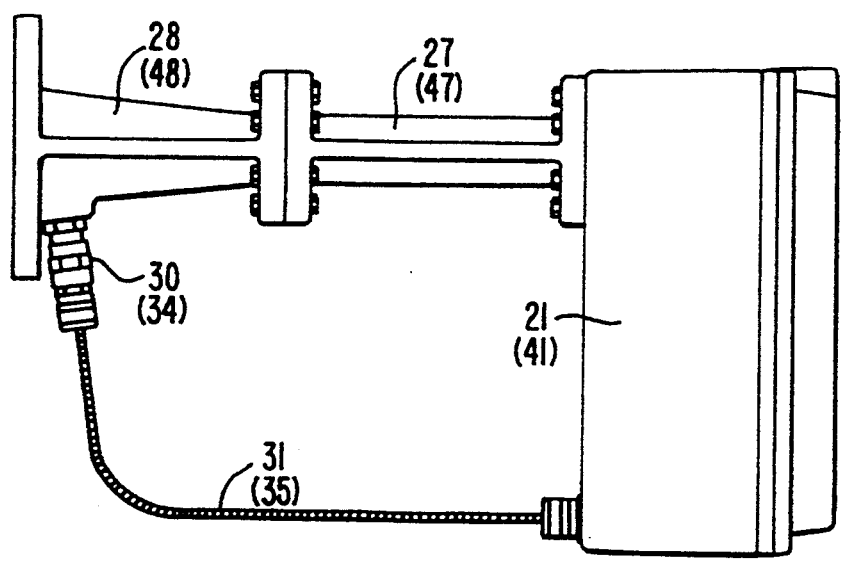
FIG. 2 is a top plan view of the sound transmitter unit.
Figure 3:
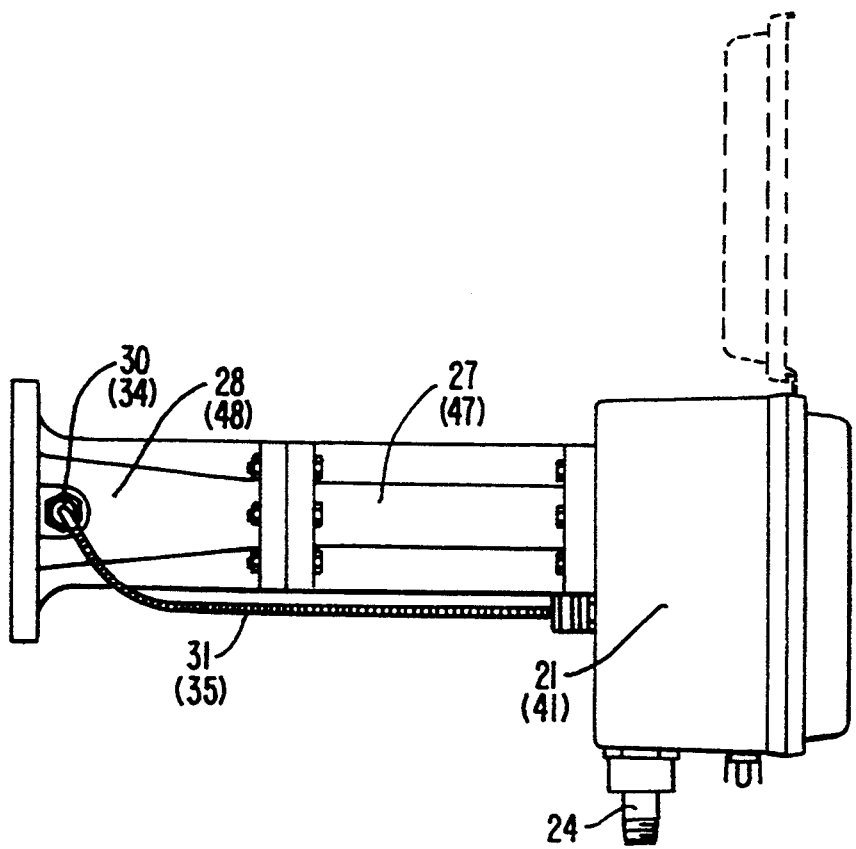
FIG. 3 is a side elevational view of the sound transmitter unit.
Figure 4:
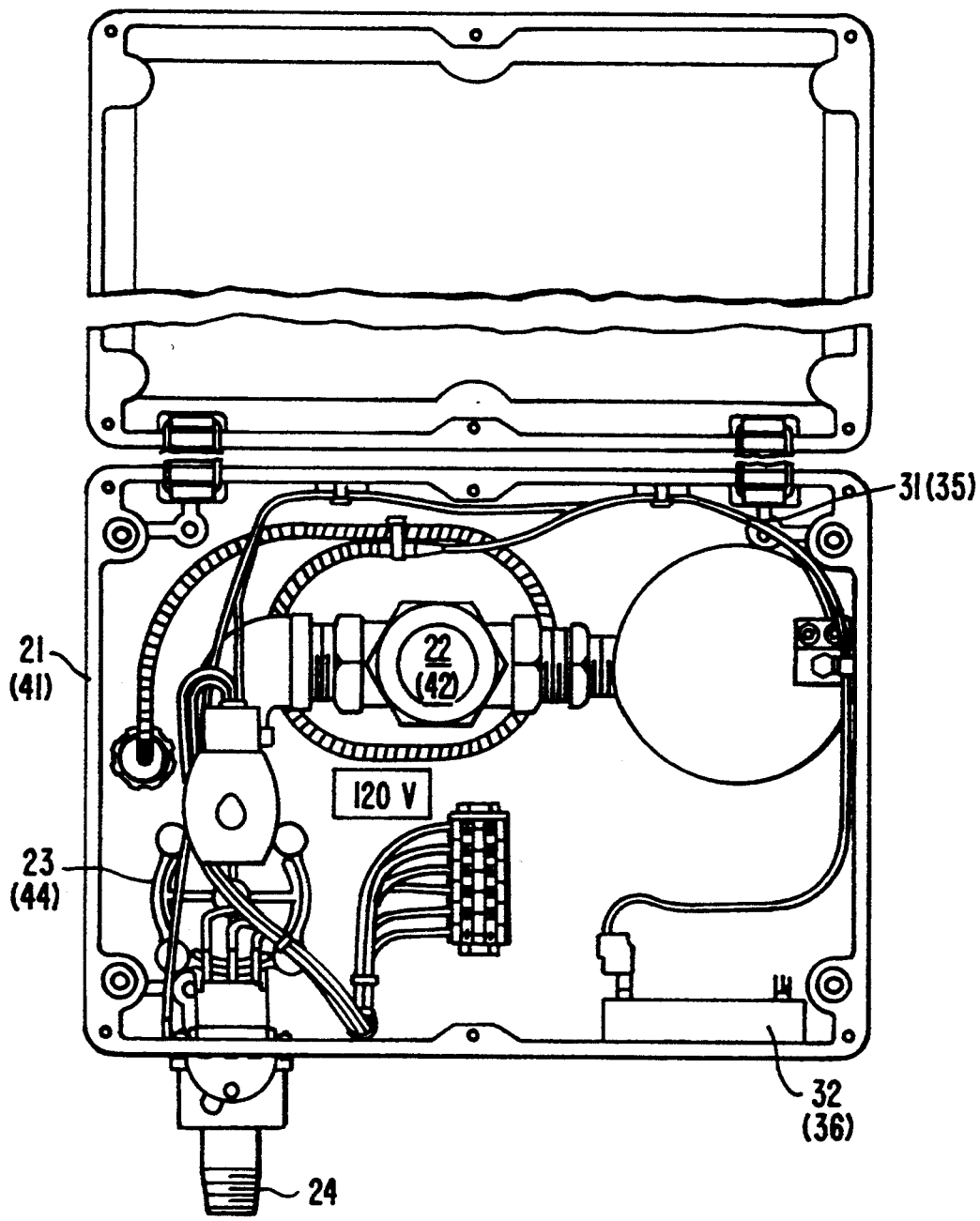
FIG. 4 is a rear elevational view of the sound transmitter unit with the cover opened.
Figure 5:
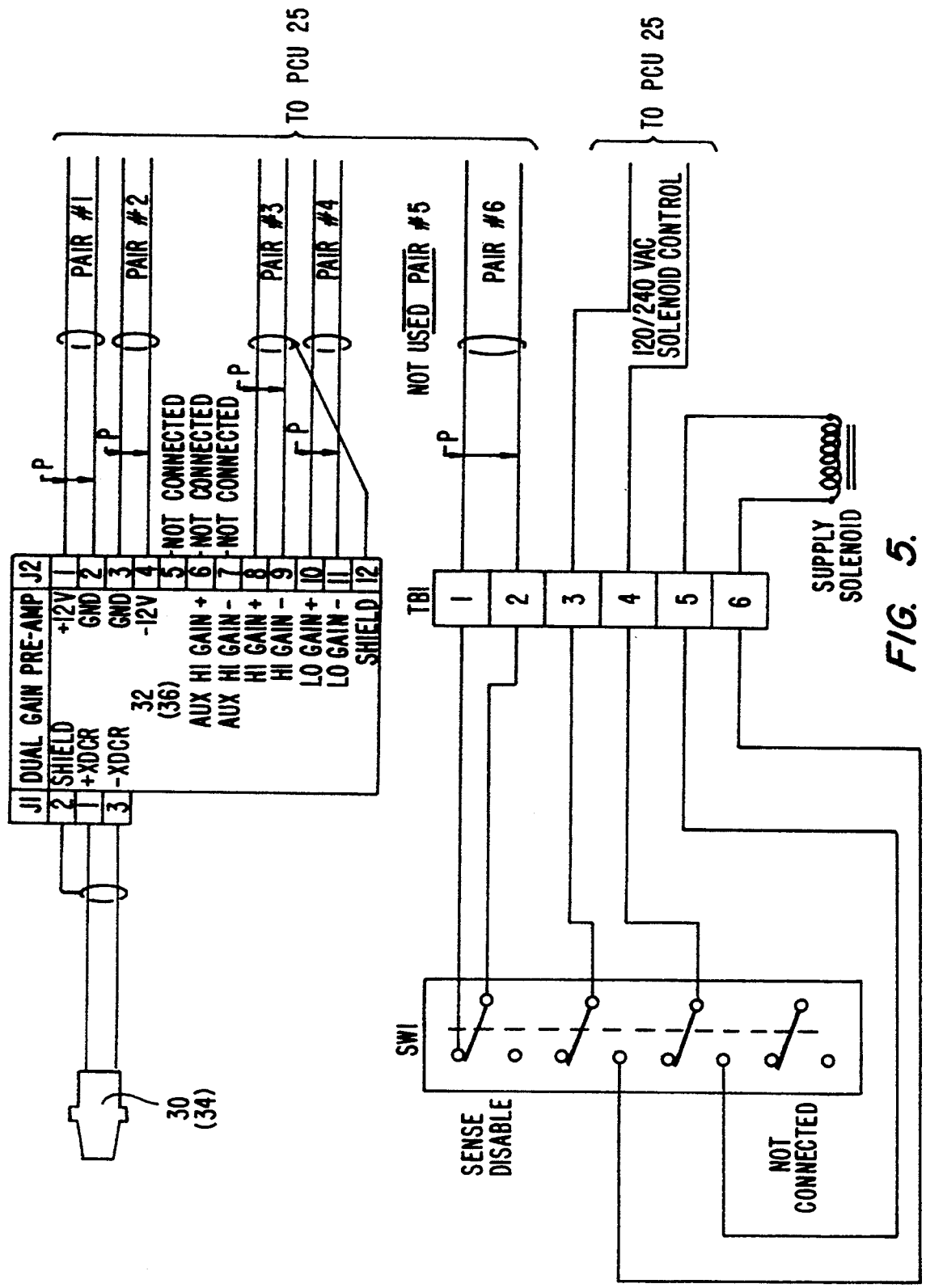
FIG. 5 is a wiring diagram of the sound transmitter unit.

Turning now to the drawings, FIGS. 1–5 illustrate a preferred embodiment of a system incorporating the invention. As seen in FIG. 1, a pair of boundary walls 11, 12 partially define a volume 14 in which a fluid (not illustrated) of interest is located. In the specific example described below, the fluid is a gas in an industrial boiler, and the parameter of interest is temperature of this gas in the volume 14. In order to determine this temperature, the transit time of acoustic waves between the boundary walls 11, 12 must be measured according to the invention.

For this purpose, a pneumatic sound generator 21 is mounted externally of wall 11 in any convenient fashion. The pneumatic sound generator 21 is a unit having two valves schematically indicated by elements 22, 23 and is designed to produce random noise in response to the application of compressed air to an inlet 24 from a suitable source shown). The compressed air is released via valve 23 which comprises an electrically operated solenoid valve (shown in FIG. 4) and which opens and closes in response to control signals supplied by a controller/processor 25. Pneumatic source 21 is coupled to the interior volume 14 via a pipe waveguide 27 having a flared end 28 coupled to a stand-off pipe coupler 29 received in a suitable aperture in wall 11. Check valve 22 (FIG. 4) prevents high pressure in volume 14 from entering the compressed air line and contaminating the compressed air conduit (or otherwise affecting adversely the sound generator 21).

The entire system is designed to produce random noise in the frequency band of interest for the acoustic pyrometry application for two major reasons: firstly, the frequency spectrum of paramount interest to acoustic pyrometry is the band of frequencies between 100 Hz and 3,000 Hz; and secondly, it is desired to have as many frequencies as possible generated in the spectrum of interest. Thus, the generator 21 causes a spectrum to be generated with acoustic energy distributed throughout the frequency band of interest.

Adjacent the flared end 28 of the pneumatic sound generator 21 is a transducer 30, which is preferably a model 941 piezoelectric transducer available from Scientific Engineering Instruments, Inc. of Sparks, Nev. and which generates electrical signals corresponding to the actual acoustic waves generated by pneumatic generator 21 and injected into the volume 14 via waveguide 27 and coupler 29. These electrical signals are coupled via a cable 31, a preamplifier 32 and cable 26 to the controller/processor 25 and represent a function x(t) required for the signal processing described below. Preamplifier 32 is a dual gain amplifier having a low gain operation and a high gain operation. The low gain operation is used for measuring the high intensity transmitting signal and the high gain operation is used for measuring a received signal.

Adjacent boundary wall 12 is a second transducer 34 which is substantially identical to transducer 30 and which generates electrical signals corresponding to the acoustic waves which travel across volume 14 and reach the region of boundary wall 12 adjacent transducer 34. The output of transducer 34 is coupled via a cable 35 and a second preamplifier 36 as a second function y(t) to controller/processor 25. Preamplifier 36 is essentially identical to preamplifier 32 in construction and function, and is used as a high gain preamplifier when used as a receiver amplifier for detecting acoustic; waves generated within the volume 14 by sound generator 21. Similarly, preamplifier 36 is used as a low gain amplifier when sound generator 41 is used as the acoustic wave generator for transmitting waves in the opposite direction towards boundary wall 11.

The system shown in FIG. 1 is designed to be symmetric about the vertical plane through the middle of volume 14. Consequently, a second pneumatic source 41, check valve 42, electrically operated air valve 44, pipe waveguide 47 and flared end 48 are provided as shown. It should be understood that such symmetry is not required for all applications, but only those applications in which it is desired to present the capability of generating acoustic waves alternately in opposite directions across volume 14.

The acoustic waves generated by source 21 or generator 41 for the high noise acoustic pyrometry application comprise a constant flow or a series of successive bursts of random acoustic waves in the frequency band of interest.

The electrical counterparts to the generated acoustic waves developed by transducer 30 and the electrical counterparts to the received acoustic waves generated by transducer 34 are coupled as functions x(t) and y(t), respectively to controller/processor 25 for further processing. This processing proceeds as follows.

An impulse response, h ($\tau$) calculation is performed on the signals x(t) and y(t). The impulse response for this system is given as the inverse Fourier Transform of the frequency response function, H(f), that: is, $$h(\tau) = F^{-1}[H(f)] = F^{-1}[S_{xy}/S_{xx}] \qquad (1)$$

where $S_{xx}(f)$ = averaged autospectral density function or autospectrum of x(t), and $S_{xy}(f)$ = averaged cross spectral density function or cross spectrum between x(t) and y(t)

It is well known that the cross-correlation function between x(t) and y(t) is given by $$R_{xy}(\tau) = F^{-1}[S_{xy}] \qquad (2)$$

As can be seen from a comparison of the two equations, the unit impulse response function resembles a cross-correlation function for an input x(t) with a uniform spectral density of $S_{xx}(f) = 1$. In effect, the unit impulse response provides the cross-correlation function for a uniform input spectral density. Hence, the input data can be computationally pre-whitened over its frequency range using a unit impulse response calculation, which improves the definition of individual propagation paths. This is an extremely important feature in acoustic pyrometry where multi-path signals are generated in the cavity of the furnace. In particular, since the actual input spectrum of the acoustic wave source extends over the relatively wide range noted above and has concentrations of power, improved resolution of flight paths can be achieved by using the unit impulse response computation. As a consequence, it is important to provide as many frequencies as possible throughout the frequency band of interest for acoustic pyrometry since each frequency generates a concentration of power for use by the unit impulse response calculation.

Figure 6:
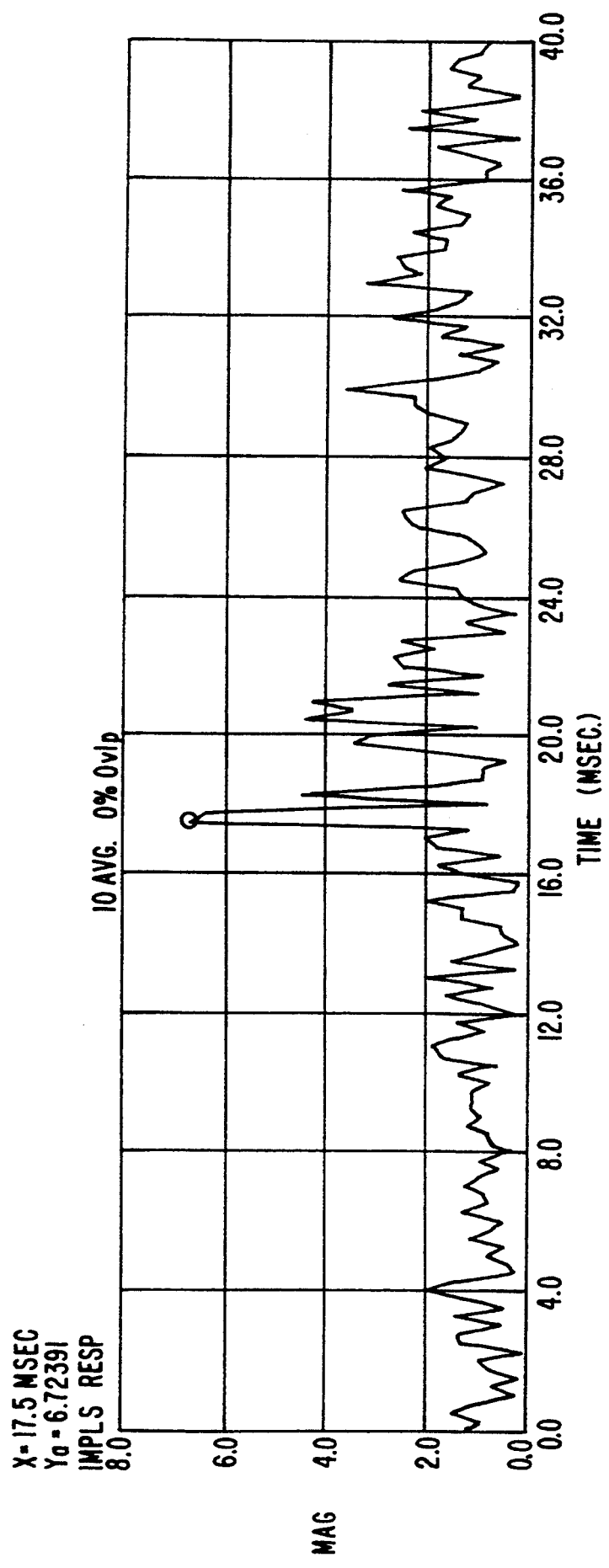
FIG. 6 is a plot of the impulse response versus time for the system of FIG. 1 applied to a boiler.

FIG. 6 illustrates the result of the impulse response computation for values of x(t) and y(t) obtained in a coal fired 265 megawatt utility boiler presenting an extremely noisy environment. This data was obtained with a pneumatic source 21 capable of generating acoustic waves in excess of 130 dB re: 20$\mu$Pa @1 m. FIG. 6 is a plot of the magnitude of the impulse response function along the ordinate versus time along the abscissa. The results show a prominent peak at a value of 17.5 milliseconds. Efforts to obtain the same pronounced data using a pulsed chirp system have been found to fail due to the level of noise in the furnace and the presence of multipaths. Other experimental results have established the advantages of the invention in obtaining reliable data in particularly noisy environments.

As will now be apparent, the invention provides a method and system for enabling the accurate determination of the transit time between two boundary points in a bounded volume of acoustic waves. From this transit time measurement, the velocity of acoustic waves in the fluid medium between the two boundaries can be computed, and the temperature and velocity of fluid (e.g., gas) can also be computed from the velocity computation using a well known relationship. Further, due to the use of a pneumatic acoustic generator 21 (and alternate, symmetric generator 41), energy levels beyond those available from electromechanical transducers can be achieved, with a corresponding increase in the ability of a system employing acoustic pyrometry to obtain reliable transit time basic information. In addition, by providing transducer 30 adjacent the entrance point of the acoustic waves into the volume 14, a reliable electrical signal replica of the acoustic waves actually injected into the volume 14 can be obtained for subsequent signal processing purposes; and an accurate replica of the received acoustic waves at the receiving wall boundary is obtained by the use of transducer 34. Consequently, intermediate effects produced by pipe 27 and flared end 28 are substantially reduced or eliminated from the information signals x(t) and y(t), which eliminates the necessity of providing compensation factors found in prior art devices using stored waveforms.

One important aspect of the invention lies in the use of the pneumatic sound generator 21 as both an acoustic wave generation device and also a contaminant purging device. In known systems, for example, using non-pneumatic generators (such as electro mechanical devices, piezoelectric transducers and the like), in particularly contaminated environments, the wave guides extending between the wave generating element (e.g., a diaphragm) and the entrance to the volume 14 can become contaminated with particulate matter found in the interior of the volume 14 (such as soot) in a coal-fired boiler system. The buildup of the contaminating particles over time leads to a change in the acoustic characteristics of the sound generating system (and the acoustic receiving system as well). Consequently, these units require cleaning at maintenance intervals whose frequency depends on a number of factors affecting the buildup of contamination. With the pneumatic sound generator described above, purging of the acoustic paths leading from the sound source to the volume under investigation is automatically performed along with the generation of the acoustic waves. The importance of this advantage is commensurate with the rate at which contamination accumulates in the system subject to the acoustic testing. For relatively clean environments, either the pneumatic generator described above or conventional acoustic wave generating devices (such as those discussed in the references cited above) may be employed.

An another significant advantage of the invention is that the effect of increasing levels of noise, which tend to mask the transit time information, can be compensated for by either increasing the length of time during which the acoustic waves are generated by the transmitter and detected by the receiver or by increasing the number of averages in the frequency domain, especially by providing an increased number of burst repetitions and corresponding impulse response computations when using the burst mode.

While the above provides a full and complete disclosure of the preferred embodiment of the invention, various modifications, alternate constructions and equivalents will appear to those skilled in the art. For example, other specific frequencies may be employed in both acoustic pyrometry applications and other applications. Also, other transducers than those specifically identified with respect to elements 30, 34 may be employed, as desired. Therefore, the above descriptions and illustrations should not be construed as limiting the invention which is defined by the appended claims.

What is claimed is:

1. A method of measuring a transit time of acoustic waves in a fluid in a noisy environment, said method comprising the steps of:
   (a) transmitting randomly generated acoustic waves through the fluid from a transmitting location to a receiving location;
   (b) coupling electrical signals corresponding to said acoustic waves transmitted from said transmitting location to a computing device;
   (c) coupling electrical signals corresponding to the acoustic waves arriving at the receiving location to the computing device; and
   (d) determining the transit time of the acoustic waves between the transmitting location and the receiving location by
      (1) obtaining the impulse response from the electrical signals corresponding to said transmitted waves and from the electrical signals corresponding to the received waves, whereby said impulse response is defined by the relationship:

$$h(\tau) = F^{-1}[S_{xy}/S_{xx}]$$

whereby
   $x(t)$ = the electrical signals corresponding to said transmitted waves
   $y(t)$ = the electrical signals corresponding to said received waves
   $X(f) \Delta F[x(t)]$
   $Y(f) \Delta F[y(t)]$
   $S_{xy} \Delta X^*Y$
   $S_{xx} \Delta X^*X$ and (2) determining the point of maximum value of the impulse response, the transit time of the acoustic waves being represented by the value $\tau$ at which the point of maximum value of the impulse response is found.

2. The method of claim 1 further including the step of computing the temperature of the fluid from the transit time determined in step (d).

3. The method of claim 1 wherein said step (a) of transmitting includes transmitting continuous acoustic waves.

4. The method of claim 1 wherein said step (a) of transmitting includes transmitting successive bursts of random acoustic waves.

5. The method of claim 1 wherein said step (a) of transmitting includes transmitting random acoustic waves having a spectrum of interest and a plurality of frequencies.

6. The method of claim 5 wherein the spectrum of interest is a band of frequencies between about 100 Hz and 3,000 Hz.

7. The method of claim 1 further including the step of computing the velocity of the acoustic waves in the fluid from the transit time determined in step (d).

8. A method of determining the temperature of a fluid in a noisy environment, said method comprising the steps of:
- (a) transmitting successive bursts of random acoustic waves through the fluid from a transmitting location to a receiving location, said waves having a spectrum of interest and a plurality of frequencies;
- (b) coupling electrical signals corresponding to said acoustic waves transmitted from said transmitting location to a computing device;
- (c) coupling electrical signals corresponding to the acoustic waves arriving at the receiving location to the computing device; and
- (d) determining the transmit time of the acoustic waves between the transmitting location and the receiving location by
  - (1) obtaining the impulse response from the electrical signals corresponding to said transmitted waves and from the electrical signals corresponding to the received waves, whereby said impulse response is defined by the relationship:

$$h(\tau) = F^{-1}[S_{xy}/S_{xx}]$$

whereby
x(t) = the electrical signals corresponding to said transmitted waves
y(t) = the electrical signals corresponding to said received waves
$X(f) \Delta F[x(t)]$
$Y(f) \Delta F[y(t)]$
$S_{xy} \Delta X^*Y$
$S_{xx} \Delta X^*X$ and (2) determining the point of maximum value of the impulse response, to transit time of the acoustic waves being represented by the value $\tau$ at which the point of maximum value of the impulse response is found and

- (e) computing the temperature of the fluid from the transmit time determined in step (d).

9. The method of claim 8 wherein the spectrum of interest is a band of frequencies between about 100 Hz and about 3,000 Hz.

10. A system for measuring a transit time of acoustic waves in a fluid in a noisy environment, said system comprising:
- transmitter transducer means for generating random acoustic waves for transmission through the fluid from a transmitting location to a receiving location;
- means for producing electrical signals corresponding to the acoustic waves generated by said transmitter transducer means;
- receiver transducer means for sensing the acoustic waves arriving at the receiving location and for producing electrical signals corresponding to the received acoustic waves; and
- computing means for receiving the electrical signals from said producing means and said receiver means and for determining the transit time of the acoustic waves between the transmitting location and the receiving location by
  - (1) obtaining the impulse response of the electrical signals corresponding to said transmitted waves and from the electrical signals corresponding to the received waves, whereby said impulse response is defined by the relationship:

$$h(\tau) = F^{-1}[S_{xy}/S_{xx}]$$

whereby
x(t) = the electrical signals corresponding to said transmitted waves
y(t) = the electrical signals corresponding to said received waves
$X(f) \Delta F[x(t)]$
$Y(f) \Delta F[y(t)]$
$S_{xy} \Delta X^*Y$
$S_{xx} \Delta X^*X$ and (2) determining the point of maximum value of the impulse response, transit time of the acoustic waves being represented by the value $\tau$ at which the point of maximum value of the impulse response is found.

11. The system of claim 10 wherein said computing means further includes means for determining the temperature of the fluid medium from the transit time.

12. The system of claim 10 wherein said transmitter transducer means includes means for generating continuous random acoustic waves.

13. The system of claim 10 wherein said transmitter transducer means includes means for generating successive bursts of random acoustic waves.

14. The system of claim 10 wherein said transmitter transducer means includes means for generating acoustic waves having a spectrum of interest and a plurality of frequencies.

15. The system of claim 14 wherein the spectrum of interest is a band of frequencies between about 100 Hz and about 3,000 Hz.

16. The system of claim 10 wherein said computing means further includes means for determining the velocity of the acoustic waves in the fluid medium from the transit time.

17. A system for determining the temperature of a fluid in a noisy environment, said system comprising:
- transmitter transducer means for generating successive bursts of random acoustic waves for transmission through the fluid from a transmitting location to a receiving location, said bursts having a spectrum of interest and plurality of frequencies;
- means for producing electrical signals corresponding to said acoustic waves generated by said transmitter transducer means;
- receiver transducer means for sensing the acoustic waves arriving at the receiving location and for producing electrical signals corresponding to the received acoustic waves; and
- computing means for receiving the electrical signals from said producing means and said receiver means and for determining the transit time of the acoustic waves between the transmitting location and the receiving location by
  - (1) obtaining the impulse response of the electrical signals corresponding to said transmitted waves and of the electrical signals corresponding to the received waves, whereby said impulse response is defined by the relationship:

$$h(\tau) = F^{-1}[S_{xy}/S_{xx}]$$

whereby x(t) = the electrical signals corresponding to said transmitted waves y(t) = the electrical signals corresponding to said received waves $X(f) \Delta F[x(t)]$ $Y(f) \Delta F[y(t)]$ $S_{xy} \Delta X^*Y$ $S_{xx} \Delta X^*X$ and (2) determining the point of maximum value of the impulse response, the transit time of the acoustic waves being represented by the value $\tau$ at which the point of maximum value of the impulse response is found;

said computing means further including means for determining the temperature of the fluid medium form the transit time.

18. The system of claim 17 wherein the spectrum of interest is in the band of frequencies between about 100 Hz and about 3,000 Hz.

19. The system of 15 wherein said transmitter transducing means includes a pneumatic driver unit.

* * * * *